US008652098B2

(12) United States Patent
Haslinger

(10) Patent No.: US 8,652,098 B2
(45) Date of Patent: Feb. 18, 2014

(54) CATHETER WITH RADIOPAQUE COIL

(75) Inventor: Thomas Haslinger, Sun City, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 0 days.

(21) Appl. No.: 13/042,792

(22) Filed: Mar. 8, 2011

(65) Prior Publication Data
US 2012/0232478 A1    Sep. 13, 2012

(51) Int. Cl.
A61M 31/00    (2006.01)
A61M 25/098    (2006.01)

(52) U.S. Cl.
USPC .................................. 604/103.1; 604/529

(58) Field of Classification Search
USPC ............... 604/103.09, 103.1, 96.01, 103.11, 604/103.12, 103.14, 104, 529
See application file for complete search history.

(56) References Cited

U.S. PATENT DOCUMENTS

| 5,630,806 | A | 5/1997 | Inagaki et al. | |
| 5,782,810 | A | 7/1998 | O'Donnell | |
| 6,285,903 | B1 | 9/2001 | Rosenthal | |
| 6,500,147 | B2 * | 12/2002 | Omaleki et al. | 604/103.09 |
| 6,702,802 | B1 | 3/2004 | Hancock et al. | |
| 6,991,626 | B2 * | 1/2006 | Wantink et al. | 604/524 |
| 2005/0148866 | A1 | 7/2005 | Gunderson | |
| 2010/0198193 | A1 * | 8/2010 | Trapp | 604/524 |
| 2010/0286664 | A1 * | 11/2010 | Haslinger | 604/533 |

FOREIGN PATENT DOCUMENTS

| EP | 1721631 A1 | 11/2006 |
| WO | 9211889 A1 | 7/1992 |
| WO | 03004085 A2 | 1/2003 |

OTHER PUBLICATIONS

The International Search Report from the European Patent Office in the corresponding International Patent Application No. PCT/US2012/027903 filed Mar. 6, 2012, dated Apr. 27, 2012.

* cited by examiner

Primary Examiner — Jason Flick
Assistant Examiner — Brooke Matney
(74) Attorney, Agent, or Firm — Fulwider Patton LLP

(57) ABSTRACT

A balloon catheter having a radiopaque coil embedded in the catheter's body corresponding to a landmark of the balloon or other location on the catheter body. The radiopaque coil can be viewed under fluoroscopy to located the balloon or other structure of the catheter. The coil can be readily inserted in the manufacturing process by inserting it between two layers that form the catheter body, and then sealing the coil inside the catheter at the desired location. This facilitates both the manufacturing process and prevents the marker from being dislodged during the manufacturing, navigation, or inflation process.

22 Claims, 4 Drawing Sheets

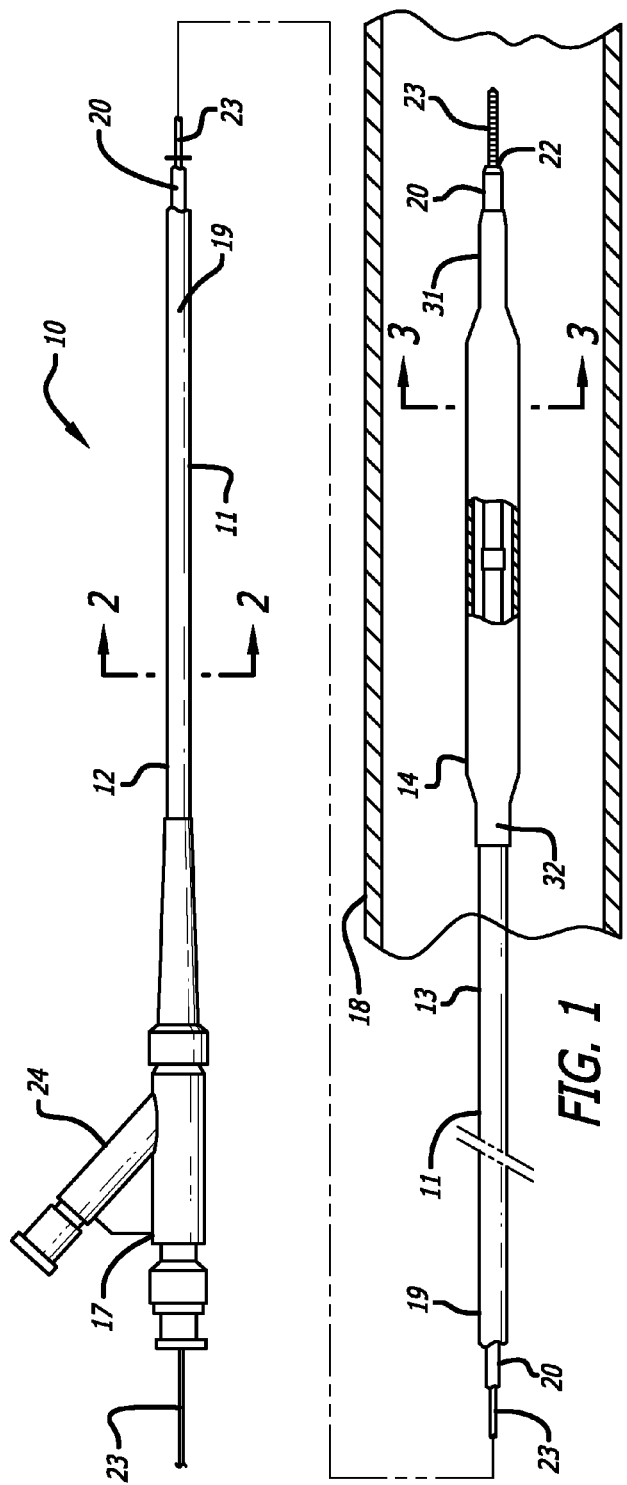
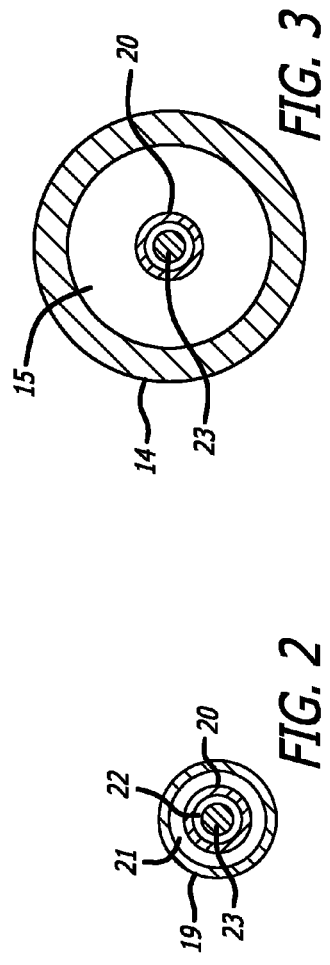

CATHETER WITH RADIOPAQUE COIL

BACKGROUND

This invention generally relates to intravascular balloon catheters and systems for performing percutaneous transluminal coronary angioplasty (PTCA) and/or stent delivery, and more particularly to a catheter delivery system that uses a radiopaque coil in the catheter structure to provide a visual indicator in the system showing where a part of the catheter is located within a body lumen.

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a pre-shaped distal tip is first percutaneously introduced into the cardiovascular system of a patient by the Seldinger technique or other method through the brachial or femoral arteries.

The catheter is advanced until the pre-shaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery over a guidewire until the balloon on the catheter is disposed within the stenotic region of the patient's artery. The balloon is inflated to open up the arterial passageway and increase the blood flow through the artery. Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed.

In a large number of angioplasty procedures, there may be a restenosis, i.e. reformation of the arterial plaque. To reduce the restenosis rate and to strengthen the dilated area, physicians may implant an intravascular prosthesis or "stent" inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is then deflated to remove the catheter and the stent is left in place within the artery at the site of the dilated lesion.

To accurately place the balloon, and also the stent, at the desired location, visual markers on the catheter are typically utilized that are read by machines outside the body. For example, in the case where a balloon catheter is used with an fluoroscope, a radiopaque marker incorporated into the catheter body may be observed visually on a screen while the procedure is taking place. In many cases, the markers must be precisely located to ensure accurate placement of the balloon in the affected area. Incorporating markers into the catheter's or balloon's structure can be expensive, and the markers can become dislodged when the catheter is torqued during delivery or when the catheter's balloon expands. For these reasons, a better and more economically feasible method of incorporating a radiopaque marker into a balloon catheter is needed.

SUMMARY OF THE INVENTION

The present invention is a catheter or catheter delivery system that incorporates a coil made from a radiopaque material that can be inserted between layers of a multi-layer catheter body. The coil is placed, for example, over a first layer of a multi-layer catheter body, and then a second layer of material is formed over the first, capturing the radiopaque coil between the two layers. Where the coil is disposed at, for example, the beginning or end of the working length of the balloon, the physician can accurately determine the precise location that the balloon needs to be positioned under fluoroscopy by locating the coil, which in turn identifies the beginning (or end) of the balloon's working length.

BRIEF DESCRIPTION OF THE DRAWINGS

FIG. 1 is an elevated, perspective view of a catheter delivery system of the present invention;

FIG. 2 is a cross-sectional view of the catheter of FIG. 1 taken along lines 2-2;

FIG. 3 is a cross-sectional view of the catheter of FIG. 1 taken along lines 3-3;

DETAILED DESCRIPTION OF THE PREFERRED EMBODIMENTS

Figure 4:
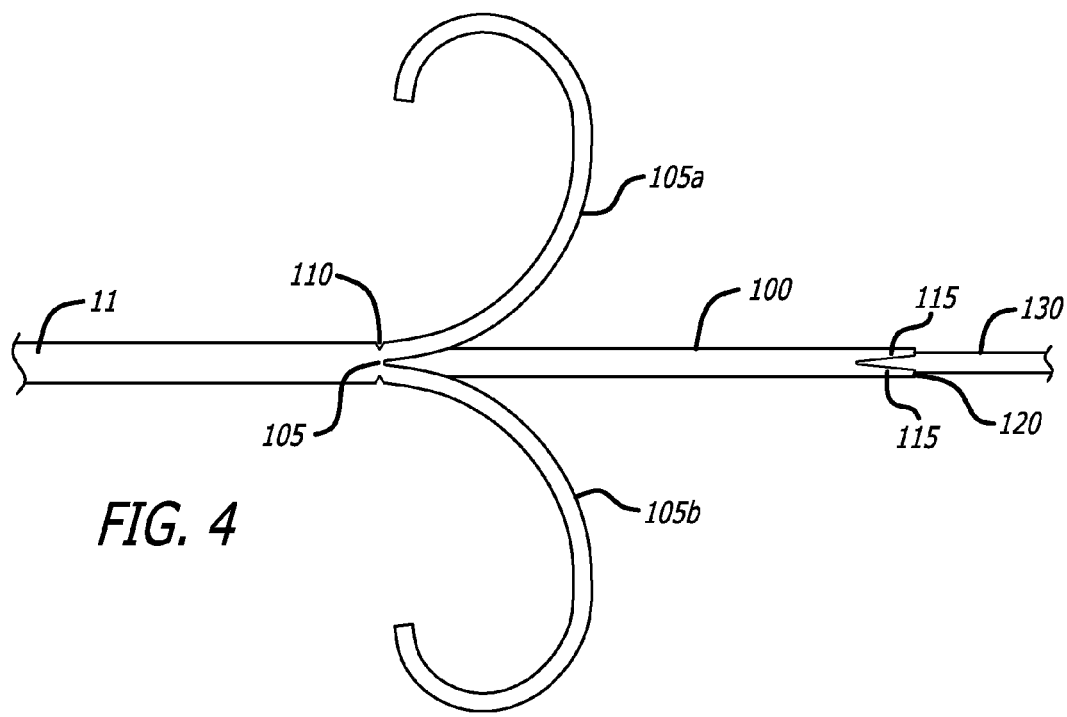
FIG. 4 is a perspective view of the catheter as the outer layer is being peeled back for removal.

FIG. 1 illustrates a balloon catheter of the type that can benefit from the present invention. The catheter 10 of the invention generally comprises an elongated catheter shaft 11 having a proximal section, 12 a distal section 13, an inflatable balloon 14 formed of one or more polymeric materials on the distal section 13 of the catheter shaft 11, and an adapter 17 mounted on the proximal section 12 of shaft 11. In FIG. 1, the distal portion of the catheter 10 is illustrated within a patient's body lumen 18, prior to expansion of the balloon 14.

In the embodiment illustrated in FIG. 1, the catheter shaft 11 has an outer tubular member 19 and an inner tubular member 20 disposed within the outer tubular member defining, with the outer tubular member, an inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity 31 of the inflatable balloon 14 is sealingly secured to the distal extremity of the inner tubular member 20 and the proximal extremity 32 of the balloon 14 is sealingly secured to the distal extremity of the outer tubular member 19.

FIGS. 2 and 3 show transverse cross sections of the catheter shaft 11 and balloon 14, respectively, illustrating the guidewire receiving lumen 22 of the guidewire's inner tubular member 20 and inflation lumen 21 leading to the balloon interior 15. The balloon 14 can be inflated by a fluid introduced at the port in the side arm 24 into inflation lumen 21 contained in the catheter shaft 11, or by other means, such as from a passageway formed between the outside of the inner tubular member 20 and the outer tubular member 11, depending on the particular design of the catheter. The details and mechanics of balloon inflation vary according to the specific design of the catheter, and are well known in the art.

Typically balloon catheters of the type shown in FIG. 1 include radiopaque markers incorporated onto the inner tubular member. These markers must be formed onto the inner tubular member's surface, either through adhesives, mechanical attachment, or embedded into the inner tubular member's material. As explained above, there are shortcomings with incorporating radiopaque markers relating to reliability of adhering the markers to the catheter body as well as the fact that the procedure is expensive and reduces the manufacturing yield of the catheters. The present invention overcomes these shortcomings by implanting a radiopaque coil into the catheter body, preferably at a location of interest to the physician, so that the conventional balloon markers can be omitted. FIGS. 4-7 illustrate the various steps of one method for constructing the catheter of the present invention.

With reference to FIG. 4, a catheter body 11 is formed on a mandrel 130 and may be formed, for example, as a dual-layer hollow extrusion with a lubricious inner layer 100 of HDPE or ultra high molecular weight polyethylene (UHMWPE) and an outer layer 105 of nylon or Pebax, with or without the usual Primacor "tie layer" that binds the inner layer 100 to the outer layer 105. To insert the radiopaque coil into the catheter body, the outer layer 105 is stripped away by peeling back tabs 115 until the scored portion 110 is readed, whereupon a coil placed over the inner layer 100. Assembly begins with the following steps to remove a distal section of the outer Pebax or nylon layer 105:

Step 1: At an appropriate distance from the distal end of the catheter body 11, the outer layer of the HDPE/nylon or HDPE/Pebax extrusion is circumferentially scored 110 using a cutting instrument such as a razor blade or the like to create a break point of the outer layer 105 only (FIG. 4). Care is called for to control the scoring blade in order to protect the inner layer 100.

Step 2: A longitudinal slit is made at the distal end of the catheter body over a length of several millimeters or more using a cutting knife such as a razor blade or equivalent, creating two semi-circular halves at the distal end.

Figure 5:
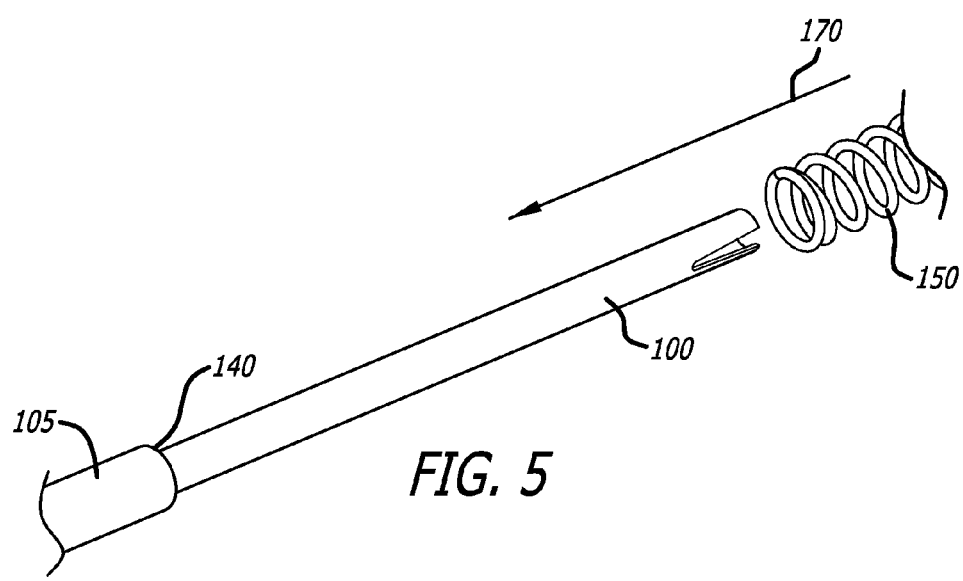
FIG. 5 is a perspective view of the coil being placed over the inner layer of the catheter.
Figure 6:
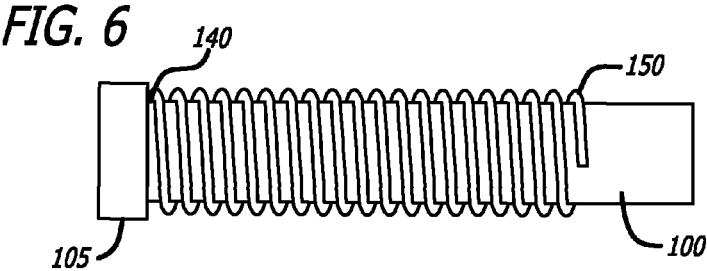
FIG. 6 is an enlarged perspective view of the coil on the inner layer of the catheter.

Step 3: To separate the outer layer 105 from the inner layer 100, both halves of the bisected end are folded or rolled back, and a grasping tool such as tweezers or the like is used to grasp the outer layer 105 at the semi-circular halves and pull them away from the inner layer 100 of each half (FIG. 4). The outer layer 105 is then peeled away from their respective inner layer to thus separate and remove the outer layer until the score mark 110 is reached, whereupon the outer layer halves 105a,b tear away from the catheter body 11. The result is a stepped transition 140 between the exposed HDPE inner layer 100 and the intact proximal remainder of the extrusion's outer layer 105 (FIG. 5).

Figure 7:
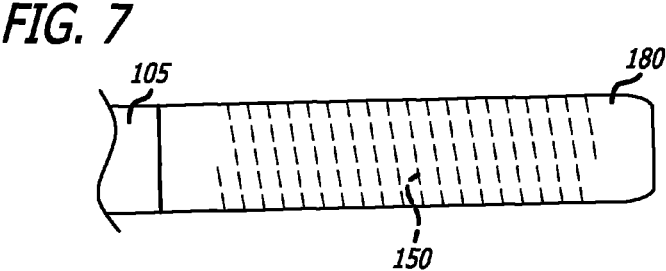
FIG. 7 is an enlarged view of the catheter with a new outer layer placed over the coil and the inner layer.

Next, a radiopaque coil 150 is slid over the exposed inner layer 100 of the catheter (see arrow 170 of FIG. 5) and a second coil may be added to the first coil. The coils 150 may, but not need be, stacked, and a separation of the two (or more) coils can provide a gap where the outer tubular member and the inner tubular member make physical contact to help seal the coil therebetween. Once the coil or coils 150 are in place, a new, lower durometer coextrusion outer layer 180 is slid over the coil(s) 150 and the inner layer 100 as shown in FIG. 7. The coextrusion 180 may include an adhesive tie-layer (not shown) to help bond the new outer layer 180 to the inner layer 100. Placing the outer layer 180 over the coil sandwiches the coil 150 inside the catheter's multi-layer construction. The new outer layer 180 is butted against the old outer layer 105, and a suitable length of shrink tubing may be placed over the joint as is known in the art. A fluoropolymer shrink tube material, such as FEP, is preferable due to its non-stick nature. This region is then progressively heated to melt bond the various segments 180 and 100 together and, where present, allow a Primacor middle layer to adhere or "tie" the outer layer 180 to the underlying HDPE layer. Afterwards, the shrink tubing and mandrel 130 are removed to leave the finished catheter body with the radiopaque coil 150 embedded in the catheter body.

Figure 8:
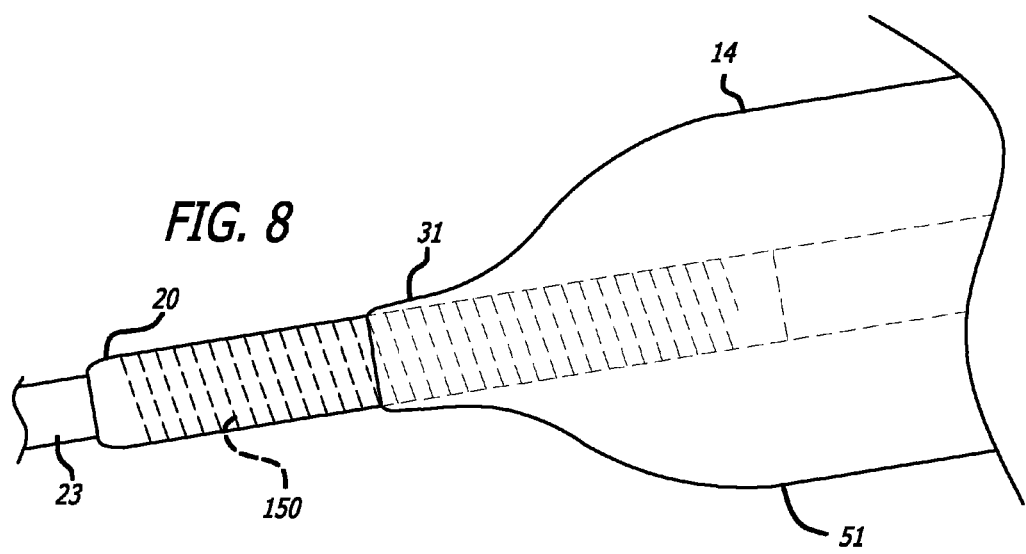
FIG. 8 is an enlarged view, partially in shadow, of the catheter with the balloon showing the position of the coil in a first embodiment.
Figure 9:
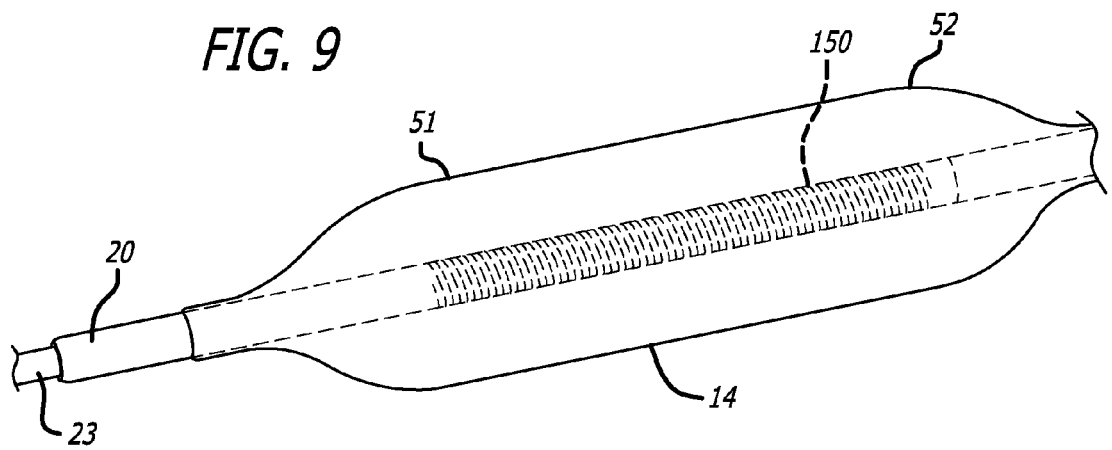
FIG. 9 is a perspective view of the catheter balloon showing the position of the coil in a second embodiment.

The resultant catheter has the radiopaque coil 150 embedded in its construction and can be used to locate the balloon 14 or other part of the catheter under fluoroscopy. In FIG. 8, the catheter 11 can be seen with a balloon 14 mounted thereon such that the coil 150 terminates at the end of the working section 51 of the balloon 14. Under fluoroscopy, a physician would be able to locate the coil 150 and immediately know where the working section 51 of the balloon ends. This feature allows the physician to locate the coil adjacent the lesion or obstruction and know with confidence that the balloon 14 will be applied at the precise location where the proximal end of the coil 150 begins. Alternatively, as shown in FIG. 9, the coil 150 or coils can be placed along and co-terminus with the working section of the balloon 14 (between 51 and 52). For the catheter balloon 14 of FIG. 9, the coil 150 corresponds to the beginning 52 and end 51 of the working portion of the balloon 14, so the physician can locate the coil 150 under fluoroscopy and place the balloon 14 precisely where it needs to be to accomplish the greatest effectiveness. Other locations are also available, such as at the beginning of the working section of the balloon for example.

The outer layer 105 can be any durometer polymer, as required by the application, and its inner layer 100 can be any extrudable lubricious material. However, preferably the layer materials should not adhere well to each other during extrusion, because peeling off the outer layer 105 at the distal end would be more difficult. The dual layer catheter may be E-beam irradiated, particularly if its inner layer is HDPE (or UHMWPE), as this promotes cross-linking and thus prevents undesirable material flow of the inner layer during subsequent melt bonding operations.

The newly added outer layer segment 180 can be any durometer polymer, as the application requires, but it is preferred that it contain an inner surface of a "tie layer" material like Primacor in order to promote secure bonding to the inner layer 100. The heat needed for such bonding is preferably achieved by equipment that provides localized and controllable heat with the ability to traverse or rotate, and the required radial pressure is preferably provided by shrink tubing which does not adhere well to the underlying materials. Although it would be possible to simply heat the assembly in an oven, this is less desirable because of a greater tendency to trap air beneath the shrink tubing leading to surface irregularities.

This invention is also applicable to inner members whose inner layer 100 is a fluoropolymer such as PTFE. For example, the inner layer 100 can be a single-layer extrusion that is subsequently etched (e.g., sodium naphthalene or "Tetra Etch") to promote bondability of its outer surface. An outer layer 105 is then extruded onto the fluoropolymer tubing in a semi-continuous (reel to reel) manner, with the extrusion parameters selected to prevent melt bonding of the two layers. Thus, the outer layer 105 can be subsequently peeled away at one end to make room for the installation of various durometers of outer jacket segments and radiopaque coils 150. In this embodiment, the added segments do not require an inner "tie layer" because they can be melt bonded directly to the etched fluoropolymer surface, again using heat and shrink tubing.

While particular forms of the invention have been illustrated and described, it will be apparent to those skilled in the art that various modifications can be made without departing from the spirit and scope of the invention. Accordingly, it is not intended that the invention be limited except by the appended claims.

What is claimed is:

1. A catheter body for insertion through a body lumen, comprising:
    an inner tubular member and an outer tubular member, at least a portion of the outer tubular member extending co-axially around the inner tubular member forming a space therebetween to create an inflation lumen, the inner tubular member having a guide wire lumen extending therethrough;
    wherein the inner tubular member includes a first layer, a second layer and a radiopaque coil inserted between the first and second layers; and
    an inflatable balloon attached to the outer tubular member which is in fluid communication with the inflation lumen, wherein the inflatable balloon has a working section in which a length of the balloon has substantially the same diameter when the balloon is inflated and the radiopaque coil is disposed on the inner tubular member and the ends of the radiopaque coil terminate near the ends of the working section of the inflatable balloon to mark the location of the working section of the inflatable balloon.

2. The catheter body of claim 1, wherein the second layer is formed in two parts.

3. The catheter body of claim 2, wherein the second layer is formed by stripping away a first section, and then forming a new section in its place.

4. The catheter body of claim 3, where the second layer is adhered to the first layer with a tie layer.

5. The catheter body of claim 4, where the tie layer is between the new section of the second layer and the first layer.

6. The catheter body of claim 1, wherein the first layer is high density polyethylene.

7. The catheter body of claim 1, wherein the first layer is ultrahigh molecular weight polyethylene.

8. The catheter body of claim 1 wherein the second layer is nylon.

9. The catheter body of claim 1 wherein the second layer is Pebax.

10. The catheter body of claim 1, wherein the first layer and the second layer are sandwiched together over the radiopaque coil by heat.

11. The catheter body of claim 1, further comprising a second radiopaque coil stacked against the first radiopaque coil.

12. The catheter body of claim 11, wherein the first radiopaque coil demarks the proximal onset of a working section of an inflation balloon and the second radiopaque coil demarks a distal end of the working section of the inflation balloon.

13. A catheter body for insertion through a body lumen, comprising:
    an inner tubular member having a guide wire lumen extending therethrough, the inner tubular member including a proximal section and a distal section, the inner tubular member having a continuous inner layer which extends from the proximal section to the distal section, a first outer layer co-axially disposed over the inner layer in the proximal section, a radiopaque marker co-axially disposed over the inner layer in the distal section, and a second outer layer co-axially disposed over the radiopaque marker and the inner layer in the distal section, the second outer layer being made from a different material than the first outer layer;
    an outer tubular member having at least a portion which extends co-axially around the inner tubular member forming a space therebetween to create an inflation lumen; and
    an inflatable balloon having one end attached to the outer tubular member and another end attached to the distal section of the inner tubular member which is in fluid communication with the inflation lumen, the inflatable balloon having a working section and the radiopaque marker having a first end disposed near one end of the working section and a second end disposed near the other end of the working section, wherein the radiopaque marker shows the location of the inflatable balloon.

14. The catheter body of claim 13, wherein the radiopaque marker is a coil.

15. The catheter body of claim 13, wherein the inner layer of the inner tubular member is made from high density polyethylene.

16. The catheter body of claim 13, wherein the inner layer of the inner tubular member is made from ultrahigh molecular weight polyethylene.

17. The catheter body of claim 13 wherein the first outer layer of the inner tubular member is made from nylon.

18. The catheter body of claim 13 wherein the first outer layer of the inner tubular member is made from Pebax.

19. The catheter body of claim 13, where the second outer layer of the distal section of the inner tubular member is adhered to the inner layer of the inner tubular member with a tie layer.

20. The catheter body of claim 13 wherein the inner layer and the first outer layer of the proximal section of the inner tubular member are co-extruded tubing.

21. The catheter body of claim 13, where the first outer layer abuts the second outer layer of the inner tubular member.

22. The catheter body of claim 13, where a length of shrink tubing is placed co-axially over the second outer layer of the inner tubular member.

* * * * *